(12) United States Patent
Hossack et al.

(10) Patent No.: US 8,057,392 B2
(45) Date of Patent: Nov. 15, 2011

(54) EFFICIENT ARCHITECTURE FOR 3D AND PLANAR ULTRASONIC IMAGING—SYNTHETIC AXIAL ACQUISITION AND METHOD THEREOF

(75) Inventors: John A. Hossack, Charlottesville, VA (US); Travis N. Blalock, Charlottesville, VA (US); William F. Walker, Earlysville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1806 days.

(21) Appl. No.: 11/245,266

(22) Filed: Oct. 5, 2005

(65) Prior Publication Data

US 2006/0100516 A1    May 11, 2006

Related U.S. Application Data

(60) Provisional application No. 60/616,176, filed on Oct. 5, 2004.

(51) Int. Cl.
*A61B 8/00* (2006.01)
(52) U.S. Cl. ........ 600/443; 600/437; 600/447; 600/453; 600/454; 600/455; 600/456; 600/457; 600/458
(58) Field of Classification Search ................... 600/437, 600/439, 443, 447
See application file for complete search history.

(56) References Cited

U.S. PATENT DOCUMENTS

| 5,638,821 | A | 6/1997 | Nakamura et al. |
| 6,254,542 | B1 | 7/2001 | Hamilton et al. |
| 6,309,356 | B1 * | 10/2001 | Ustuner et al. ............... 600/443 |
| 6,344,023 | B1 | 2/2002 | Fukukita et al. |
| 6,551,246 | B1 * | 4/2003 | Ustuner et al. ............... 600/447 |

OTHER PUBLICATIONS

International Search Report for International Application No. PCT/US2005/36077.

* cited by examiner

*Primary Examiner* — Tse Chen
*Assistant Examiner* — Baisakhi Roy
(74) *Attorney, Agent, or Firm* — McDonnell Boehnen Hulbert & Berghoff LLP

(57) ABSTRACT

An improved device and method for collecting data used for ultrasonic imaging. The data is gathered over numerous transmit and echo receive cycles, or iterations and combined into a synthetic acquisition representing a complete echo characteristic acquisition. At each iteration, only a portion, or subset, of the echo characteristic is sampled and stored. During the iterations, the portion of the echo characteristic that is measured and sampled is varied by changing the relative sampling instants. That is, the time offset from the transmission to the respective sampling instant is varied. The sample sets representative of the entire echo characteristic are then compiled from the multiple subsets of the ultrasonic transmissions.

30 Claims, 8 Drawing Sheets

EFFICIENT ARCHITECTURE FOR 3D AND PLANAR ULTRASONIC IMAGING—SYNTHETIC AXIAL ACQUISITION AND METHOD THEREOF

GOVERNMENT RIGHTS

The United States Government may have acquired certain rights in this invention pursuant to Grant No.: EB02349 awarded by the National Institutes of Health (NIH).

CROSS-REFERENCE TO RELATED APPLICATIONS

The present application claims priority to U.S. Provisional Application No. 60/616,176, filed Oct. 5, 2004, entitled "Efficient Architecture for 3D and Planar Ultrasonic Imaging—Synthetic Axial Acquisition and Method Thereof", which is hereby incorporated by reference herein in its entirety.

This application is also related to International Application No. PCT/US03/06607, filed Mar. 6, 2003, entitled "An Intuitive Ultrasonic Imaging System and Related Method Thereof," and corresponding U.S. patent application Ser. No. 10/506,722 filed Sep. 7, 2004 of which are assigned to the present assignee and are hereby incorporated by reference herein in their entirety. The present invention may be implemented with the technology discussed throughout aforementioned International Application No. PCT/US03/06607 and U.S. patent application Ser. No. 10/506,722.

The present application is also related to PCT International Application No. PCT/US04/00888, filed Jan. 14, 2004, entitled "Ultrasonic Transducer Drive," of which is assigned to the present assignee and is hereby incorporated by reference herein in its entirety. The present invention may be implemented with the technology discussed throughout aforementioned International Application No. PCT/US04/00888.

The present application is also related to PCT International Application No. PCT/US04/00887, filed Jan. 14, 2004, entitled "Ultrasound Imaging Beam-former Method and Apparatus," of which is assigned to the present assignee and is hereby incorporated by reference herein in its entirety. The present invention may be implemented with the technology discussed throughout aforementioned International Application No. PCT/US04/00887.

The present application is also related to PCT International Application No. PCT/US2004/001002, filed Jan. 15, 2004, entitled "Efficient Ultrasound System for Two-dimensional C-Scan Imaging and Related Method thereof," of which is assigned to the present assignee and is hereby incorporated by reference herein in its entirety. The present invention may be implemented with the technology discussed throughout aforementioned International Application No. PCT/US04/US2004/001002.

FIELD OF THE INVENTION

The present invention relates to ultrasound imaging devices and techniques. More specifically, the various embodiments of the present invention provide a novel beam-forming strategy and system architecture that may be used to form either 2D C-scan images or 3D images using a 2D transducer array. Additionally, the system and methods may be used to form b-scan images, and A-Mode data.

BACKGROUND

Medical imaging is a field dominated by high cost systems that are so complex as to require specialized personnel for operation and the services of experienced physicians for image interpretation. Medical ultrasound, which is considered a low cost modality, utilizes imaging systems costing as much as $250K. These systems are operated by sonographers with several years of training or specialized physicians. This high-tech, high-cost approach works very well for critical diagnostic procedures. However it makes ultrasound impractical for many of the routine tasks for which it would be clinically useful.

The block diagram of a conventional phased array ultrasound system 10 is shown in FIG. 1. A piezoelectric transducer array 12 (or using alternative electrical/ultrasound transduction mechanism—e.g. capacitive micro-machined devices), shown on the left, acts as the interface to the body by converting electrical signals to acoustic pulses and vice versa. Image formation begins when the states of the transmit/receive switches (TX/RX switches 14) are altered to connect the transducer elements to individual transmit generators TX 16. The transmit generators 16 output time varying waveforms with delay and amplitude variations selected to produce a desired acoustic beam. Voltages of up to approximately 150 Volts are applied to the transducer elements. Once transmission is complete, the state of the TX/RX switch 14 is changed to connect the receive circuitry to each element. Incoming voltage echoes are amplified by preamplifiers (preamp 18) and Time Gain Control (TGC 20) circuits to compensate for signal losses associated with diffraction and attenuation. Next, sample and hold circuits (S/H 22) and analog to digital converters (A/D 24) digitize the signals. Finally, the signals are dynamically delayed and summed within one or more custom integrated circuits 26 to yield a single focused Radio Frequency (RF) echo line. This signal forms the basis of one image line.

While conventional beamforming approaches produce high quality images, they also impose significant restrictions on the use of ultrasound. The 40 Msample/s S/H and A/D circuits employed by these systems, and the high data rates they engender, result in high system cost and complexity. A modern state-of-the-art imaging system may cost as much as $250,000 and require weeks or months of user training to produce the highest quality images. Furthermore, while the transducers used by these systems are typically only a few centimeters on a side, the electronics required to form images resides in a box with dimensions on the order of 2'×3'×4'. Thus, while ultrasound systems are certainly portable, they are far from the scale that would allow each clinician to carry one in a pocket.

The applicability of conventional ultrasound is further limited by the typical image format used. Images are produced in what is commonly referred to as a B-Mode format, representing a tomographic slice through the body perpendicular to the skin surface. This image format is non-intuitive and the act of mentally registering the B-Mode image to the patient's anatomy requires significant experience.

Significant reductions in system cost and complexity have occurred over the last five years. Some of the more notable advances have been demonstrated by Sonosite. Its most recent product, which sells for approximately $12,000, produces B-Mode and color flow images using a hand-held system. This system produces good quality images and will certainly broaden the applications for ultrasound in medicine. Unfortunately, the Sonosite architecture and strategy does not appear to be capable of extension to real-time 3D imaging. Furthermore, the B-Mode image format produced by the Sonosite system and all other conventional systems is not intuitive to most first-time ultrasound users. Novice users often have difficulty mapping the image displayed on the screen to the tissue lying beneath the transducer. This most likely results from the distance (a few feet) and orientation differences between the target and image.

Ultrasonic imaging has the potential to be a common component of nearly every medical examination and procedure. But the complexity and expense of the existing ultrasound systems are an impediment to its widespread use. Consequently, an improvement is desired.

SUMMARY

The present invention provides an improved device and method for collecting data used for ultrasonic imaging. The data is gathered over numerous transmit and echo receive iterations and combined into a synthetic acquisition representing a complete echo characteristic acquisition. At each iteration, only a portion, or subset, of the echo signal is sampled and stored. During the iterations, the portion of the echo characteristic that is measured and sampled is varied by changing the relative sampling instants. That is, the time offset from the transmission to the respective sampling instant is varied. The sample sets representative of the entire echo characteristic are then compiled from the multiple subsets of the ultrasonic transmissions. Thus, rather than obtaining an entire set of echo samples needed for image processing from each echo, the method described herein performs synthetic acquisition via data collection iterations by transmitting an ultrasonic pulse, and receiving a pulse echo at a plurality of array elements, and at each element, obtaining a pulse echo sample subset at a respective time offset, wherein the time offset is varied. Then, for each of the relevant array elements, the sample subsets are used to compile a single synthesized composite pulse echo sample set that is representative of an echo characteristic at that element at a desired effective sampling rate.

In one embodiment, the pulse echo sample subset contains a single sample. The single sample may be a real valued sample, or may be a complex valued sample obtained by sampling the output signals from a demodulation circuit. Complex samples can also be approximated by combining two real samples separated by a quarter period of the echo signal's center frequency. This is referred to as "Directly Sampled In-phase and Quadrature", or DSIQ (See K. Ranangathan, M. K. Santy, J. A. Hossack, T. N. Blalock and W. F. Walker 'Direct sampled I/Q beamforming for compact and very low cost ultrasound imaging', IEEE Transactions on Ultrasonics, Ferroelectrics and Frequency Control, Vol. 59, No. 9, pp. 1082-1094 (2004), the contents of which are incorporated herein by reference).

Alternatively, the subset may be a plurality of samples. A subset having a plurality of samples may be obtained by full-rate sampling of the echo signal for a portion of the echo. In this embodiment, each subset contains no more than half the desired samples. In one embodiment, each subset contains no more than six consecutive samples.

In an alternative embodiment, the plurality of samples in each subset may be obtained by sampling at a rate lower than the desired effective sampling rate, and then interleaving the samples from multiple subsets. In some embodiments the desired effective sampling rate may be much higher than the Nyquist rate, and even the lower-rate sampling may be greater than the Nyquist rate. But in alternative embodiments operating at a desired effective sampling rate of one or two times the Nyquist rate, this likely will result in sub-Nyquist rate sampling to obtain each subset. That is, samples may be obtained from a single echo signal at rate below the Nyquist rate. Certainly this is the case where a single sample per transmit event is obtained. In subsequent iterations, samples (also at a sub-Nyquist rate) are obtained, where the sampling instants have a different time offset.

In both cases (successive sampling or sub-Nyquist sampling), the subsets are then combined to obtain to a full-length sample set representing the echo characteristic, sampled at an effective rate of at least the Nyquist rate. For embodiments using successive sampling, the sample subsets are concatenated into a single record for each element, whereas for embodiments using sub-Nyquist sampling, the sample subsets are interleaved to obtain the full echo characteristic sample record. The beginning and ending time offsets are determined in large part by the tissue depth of the desired image.

In some preferred embodiments, every element in the array is used to obtain sample subsets. In other embodiments, only some of the array elements are used to obtain samples during a given iteration. For example, in some embodiments, the pulse echo sample subsets are obtained from shared sampling hardware resources. In one such embodiment, a single analog to digital converter is shared between two or more elements. In this case, more than one transmit pulse is required in order to obtain one subset for each array element. In this case, the number of array elements used in a given iteration depends on how many elements are assigned to a single converter. This is also referred to as a hardware reuse factor. For example, a hardware reuse factor of two means that two elements share resources, and thus one half the elements are able to obtain sample subsets during any given iteration.

The step of aggregating the pulse echo sample subsets of varied offsets into a single synthesized composite pulse echo sample set may be performed by concatenation or interleaving, as described herein, or it may also include manipulating the sample subsets in response to at least one motion estimation value as well as the respective time offsets used to gather the data.

In this regard, one or more array elements may be used to obtain samples used for motion estimation. A single motion estimate may be obtained from individual direct-sampled complex echo samples taken over a plurality of iterations from a single element, each sample having the same time offset. Alternatively, multiple motion estimation values may be derived from samples taken from elements that are at different locations within the array. In this manner, the motion may be evaluated for different regions of the array to accommodate tipping of the array as might occur when pressed against the tissue to be imaged. These may be referred to as regional motion estimation values. The regional motion estimation values may then be used to generate array-element specific motion estimation values.

In an alternative embodiment, echo sample subsets that overlap in time may be gathered at each iteration. That is, the time offsets at each iteration are adjusted such that the relative sampling instants have substantial overlap. In this way, the synthesized echo record may be compiled from the subsets, and in addition, consecutive echo sample subsets may be used to estimate motion. This data collection mechanism may be used at a single array element, regional array elements, or all array elements.

However obtained, the motion estimation value(s) may be used to enable/disable image processing to prevent the display of distorted images caused by excessive motion. Alternatively, the motion estimation value(s) may be used to alter or manipulate the data samples when forming the synthesized echo response characteristic in order to compensate for the motion.

One preferred method described herein performs multiple transmit firings of ultrasonic waveforms from an ultrasonic transducer array of transducer elements; after each transmit firing, a subset of echo samples of an ultrasonic echo is obtained at each of a plurality of transducer array elements, wherein each subset is a portion of a desired echo response as determined by a time offset; an equivalent full set of echo samples is retrospectively formulated from the subsets for each of the plurality of transducer array elements.

Application of the methods described herein will allow useful ultrasound systems to be produced at an extremely low cost. By eliminating many of the custom integrated circuits used in conventional systems and by altering the beamforming algorithm to enable implementation in off the shelf programmable DSP chips, this will also dramatically reduce the size of imaging systems. The potential impact in health care is broad and significant. We have identified a few possible clinical applications of this approach, although we believe that others will become apparent as clinicians gain access to the device.

These as well as other aspects, advantages, and alternatives will become apparent to those of ordinary skill in the art by reading the following detailed description, with reference where appropriate to the accompanying drawings.

DETAILED DESCRIPTION

Figure 1:
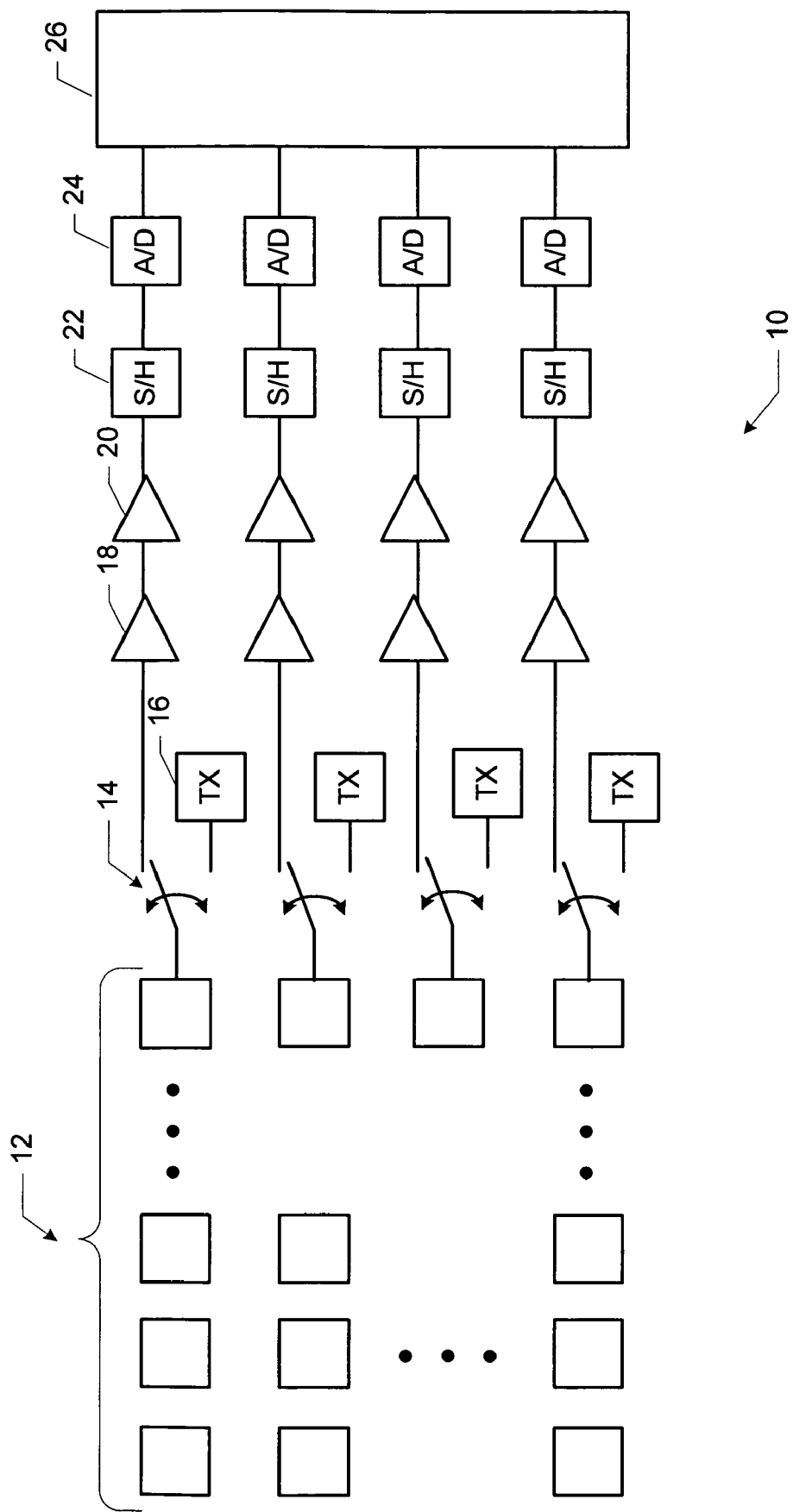
FIG. 1 is a block diagram of a prior art transducer array and data sampling hardware.
Figure 2:
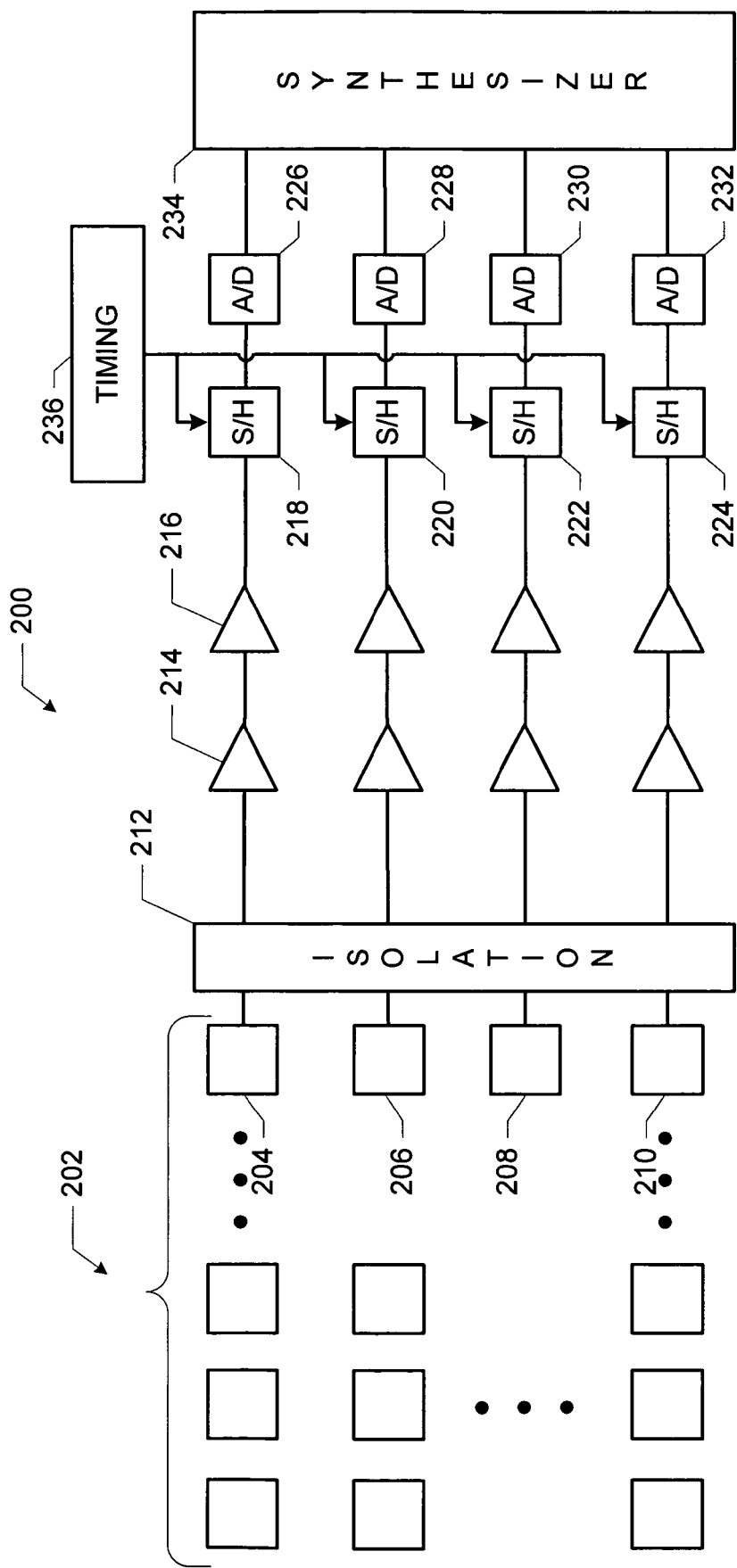
FIG. 2 is a block diagram depicting functional components of a transducer and associated sampling hardware resources arranged to implement an exemplary embodiment of the invention.

With respect to FIG. 2, a device 200 used to gather data over numerous transmit and echo receive cycles, or iterations, is shown. Array 202 of transducer elements provides the transmit and receive interface to the tissue. A single column of elements 204, 206, 208, 210 is shown, with the understanding that all elements are similarly connected to respective circuitry. Isolation circuit 212 provides isolation of the receive circuitry, and may take the form of isolation switches, as described with respect to FIG. 1. (Note that the transmit generators are not shown). The transducer elements preferably provide an unfocused planar ultrasound wave propagating into the object being imaged. As described in one or more of the related applications identified above, this strategy advantageously results in a simplified hardware configuration. In addition, receive focusing alone can achieve reasonable spatial and contrast resolution, while preserving an acceptable signal to noise ratio (SNR).

However, alternative embodiments may utilize conventional transmit beam focusing techniques, such as using time varying waveforms with delay and amplitude variations selected to produce a desired acoustic beam. In preferred embodiments using transmit beam focusing, a relatively small number of relatively wide transmit foci are used so as to cover the required field of view with a small number of discrete transmit foci. In alternative embodiments where wide transmit foci are not used, the time of acquisition becomes larger, and may result in a lower frame rate.

Each receive channel has a preamplifier 214 that is preferably impedance matched to the transducer element to maximize sensitivity and bandwidth. An additional amplifier 216 takes the place of the TGC used by conventional systems. Because only a subset of samples of the echo waveform is obtained per each transmit event, the rapid gain adjustments typical in TGC circuits are unnecessary, and may thus be optionally omitted. Next the signal enters S/H circuits 218, 220, 222, 224 which sample data over a few nanoseconds (ns) and hold their outputs for as long as one millisecond (ms).

The sampling instants are determined by timing circuit 236. In the embodiment shown in FIG. 2, each receive channel operates on the same timing signal, and hence obtains samples at the same time offset. That is, the sampling instant is the same across all elements, and is varied from iteration to iteration. Preferably, the earliest sampling instant is determined by the depth of the target to be imaged, and the sampling instant is delayed for each successive iteration by increasing the time offset by a single sampling interval. The outputs are then digitized by analog to digital (A/D) converters 226, 228, 230, 232. Sampling may thus be performed once per transmit event.

In some embodiments, it may be desirable to obtain an image where the C-plane is not parallel to the transducer face. In this case, the round trip times to the various locations on the target image plane are calculated and used as the basis of the time offsets (i.e., sampling delays) used to capture the records. In this case, the time offsets provided by timing circuit 236 are adjusted accordingly, and are not the same for all transducer array elements, although they may be the same for each row or column, depending on the orientation of the desired C-plane to the transducer array. Thus, in this case, the initial sampling instant may be adjusted for each element, as well as the particular sampling instants.

Finally, the samples are provided to the synthesizer 234, where the samples are compiled and used to formulate a complete set of samples representative of an echo characteristic. Subsequently, the sample sets are delayed and summed within a DSP, ASIC or other circuitry to yield a single focused Radio Frequency (RF) echo line. The simplest beamforming strategy is to apply complex weightings to each element signal and then sum these to focus and calculate an individual image pixel. This signal forms the basis of one image line. For a C-Scan image, this one A-line (as is known in the field) is condensed to a single pixel location in the C-Scan image. The single pixel value may be a single selected value from within the A-line data—i.e. the sample corresponding to the depth of the plane of interest. Alternatively, the sample may be interpolated from nearby samples or a composite (average—weighted or unweighted) of either pre or post envelope detected data. Generally, in the C-Scan format it is not necessary to dynamically update the receive focusing delays as a function of signal depth since the signal depth is small and required (optimal) delays change by small amounts. Nevertheless, in some situations where the depth of image formation is significant, dynamically updated receive delays (as is well known in field) are used. The apodization weights applied to the individual element signals may also be dynamically updated. Apodization is the well known approach of applying a distribution of weighting factors to the individual element signals prior to summing to produce an improved beampattern—generally having lower sidelobe levels.

Figure 6:
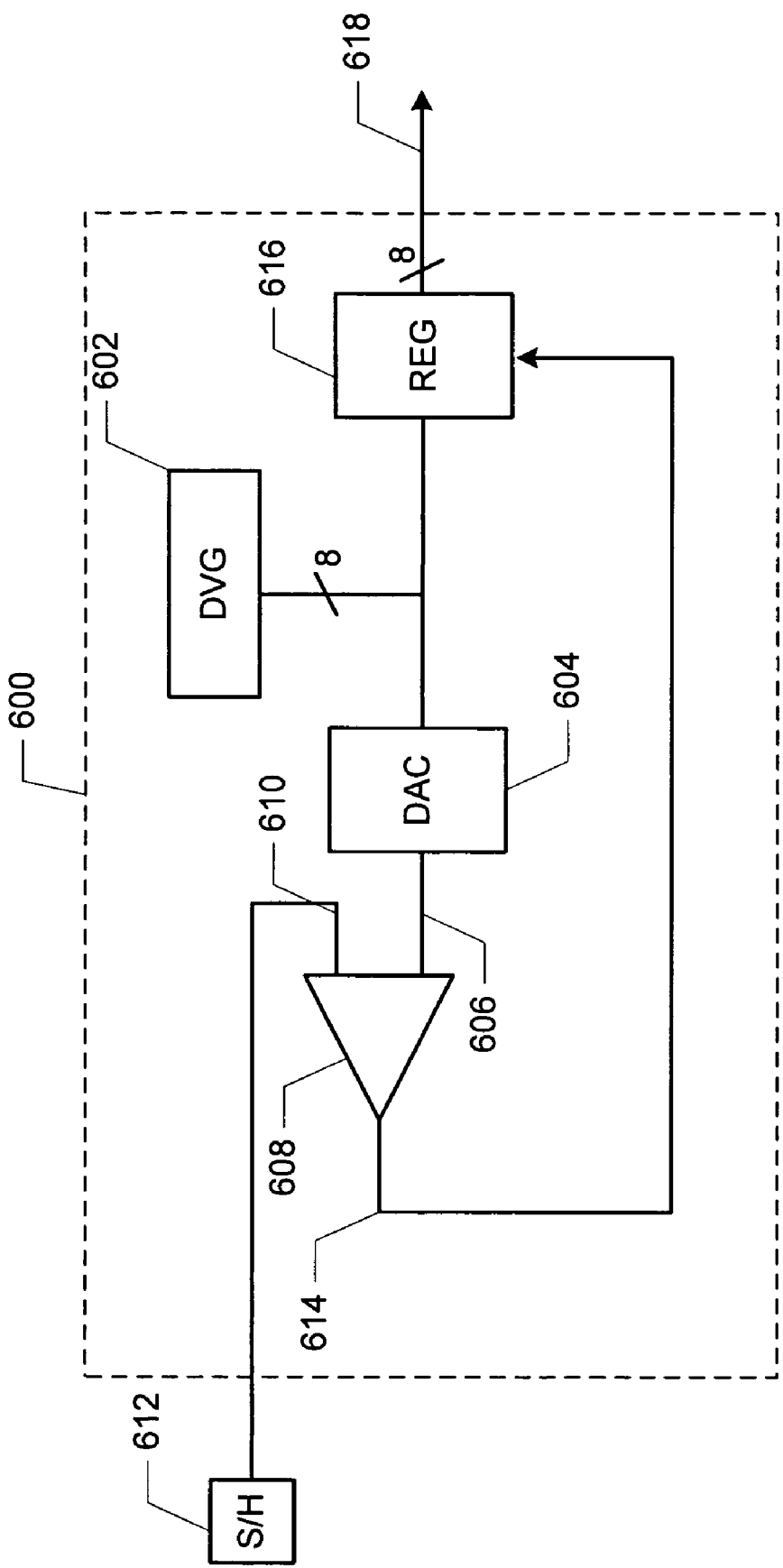
FIG. 6 is a block diagram of an exemplary embodiment of a simplified A/D converter.

Because only a small number of sampling operations (perhaps even one) per element is performed per transmit event, the A/D design is much simpler and the resultant data rate is significantly lower than for a comparable conventional prior art system. One exemplary A/D converter 600 using simplified hardware is shown in FIG. 6. A digital value generator (DVG) 602 is used to provide increasing digital values (e.g., 8 bits) to Digital to Analog Converter (DAC) 604. The DVG 602 may be a simple counter, a microprocessor, or other suitable circuitry. The DAC 604 provides an analog voltage on output 606 proportional to the binary input. The output voltage is input to comparator 608, along with the sampled voltage on line 610 from S/H circuit 612. As the voltage on DAC output 606 passes the voltage on line 610 from S/H circuit 612, the comparator output 614 changes state, and activates register 616 to load the digital value from the DVG 602. The digital conversion value is provided on A/D output 618. The A/D converter may take other forms, and FIG. 6 is merely one of many circuits known to those of skill in the art. One reason that simplified A/D converters may be used herein is due to the additional time available to digitize the sample. In the converter 600 for example, numerous clock cycles may be used as the DVG generates new digital values for conversion to an analog voltage. That is, the acquisition techniques described herein provide relief from the constraints imposed by full-rate continuous sampling over the entire echo signal of interest.

Digitized data may be temporarily stored in registers in the synthesizer 234, which may be implemented as a custom IC before being read out by a programmable digital signal processor (DSP). Alternatively, the synthesizer 234 may also be implemented on the DSP, along with the image processing.

It is also possible for the beamforming process to be applied on the received samples and then perform the assembly into finite length records in the post beamforming (beamsum) register. In this mode of operation, individual samples are delay compensated and used to populate an accumulating beamsum register (i.e. a register which adds new values to current values in the correct register location.) which adds in isolated samples from successive transmit events. Over the set of firings, the process will progressively populate the beamsum register, in a type of pipelining operation. (Alternatively, if the output is not fully populated, then values intermediate between populated values are filled by interpolation between the populated values.) This process is presented an alternative preferred embodiment. The relative merit of various processing approaches is related to the relative cost of delay processing and memory. In addition, the time required to render an image may be reduced since the beamforming process may begin before all of the data samples have been acquired. The approach used in this embodiment may not work as well in the context of inter sample interpolation—i.e. in practice, it would require a higher sampling rate because the beamforming approach suggested here is based on nearest neighbor delay operations as opposed to interpolated, or phase corrected, delays.

Figure 3:
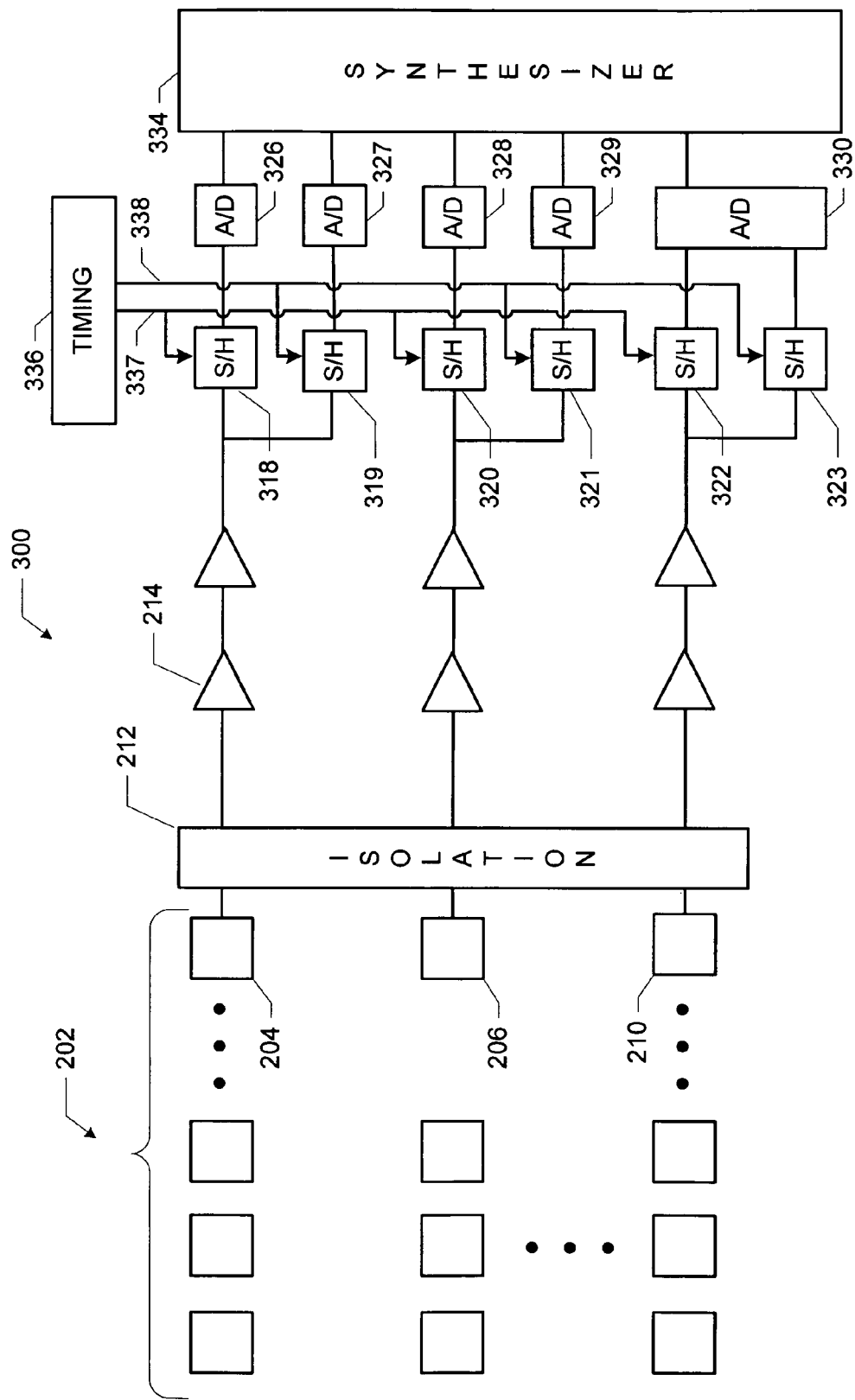
FIG. 3 is a block diagram depicting an alternative embodiment of the sampling hardware to obtain either approximate complex samples (DSIQ) or multiple samples per subset.

In an alternative embodiment shown in FIG. 3, hardware is provided to acquire multiple samples per transmit event. Note that for convenience, only three receive channels are depicted. The hardware of FIG. 3 may be configured to obtain a single complex valued sample at each sampling instant. As described in the related applications set forth above, a good approximation of a complex sample may be obtained by obtaining two real samples offset by a quarter wavelength of the center frequency of the transmitted waveform. Thus, each receive channel includes a pair of S/H circuits 318/319, 320/321, 322/323, and associated A/D circuits. The timing circuit 336 generates two timing signals, one on line 337 having the desired time offset, and one on line 338 that occurs one quarter cycle later.

In other embodiments, standard demodulation techniques are used to obtain complex sample values. That is, the echo signal may be formed into inphase and quadrature components by channeling the echo signal into two paths and mixing each of (multiplying) them with inphase and quadrature reference signals respectively. The two signals are then low pass filtered to eliminate the sum frequency components. As is known to those of skill in the art, the low pass filtered signals may represent a baseband version of the echo. Samples of this signal may then be acquired as complex samples described herein, and are representative of the magnitude and phase of the echo signal. Alternatively, the echo signal may be mixed down to an intermediate frequency (IF) and sampled as described herein. In this case, the samples may be real valued, or may be further processed by a DSP to obtain complex samples, or the DSIQ sampling technique may be applied, where the one quarter period offset is determined by the center frequency of the IF signal. Note also that DSIQ samples may be obtained from samples taken from different points (e.g., three quarters offset) or even different cycles of the waveform, as long as the timing of the sampling has the appropriate quadrature phase relationship. Of course, complex samples may be generated from DSIQ samples taken at other offsets, but one-quarter or three-quarter period offsets (or multiples thereof) provide orthogonal measurements (resulting from the sine/cosine sinusoid decomposition) making complex sample generation more computationally efficient. In this way, it is possible to accumulate finite time records of any of: real radio frequency data, complex baseband data (via standard demodulation) or DSIQ data.

Note that the A/D circuits may be provided in pairs as shown by A/D circuits 326/327 and 328/329, or alternatively, a single A/D circuit 330 may be shared by the two S/H circuits 322/323, with the sample conversion being applied serially.

In another configuration, the hardware of FIG. 3 may be used to obtain two real-valued samples separated by a single sample interval. In particular, timing signals on line 337 and 338 may be generated to cause S/H circuits 318 and 319 to sample the receive echo waveform at two separate time offsets, thereby resulting in a echo sample subset of two samples per iteration. The samples may be of consecutive sampling instants, or may be separate by two, three, or any number of sample intervals. In the embodiment of FIG. 3 configured to provide two samples per subset (i.e., per iteration), the entire record may be synthesized from a number of iterations equal to one half the desired record length. Thus, in this embodiment, the system is capable of performing the data acquisition in only two iterations: one half of the samples are gathered from one burst, and half of the samples are gathered on the second burst. The sample subsets may be obtained at full rate and then concatenated, or the two halves may be obtained at half the desired effective sampling rate, and then interleaved. In other embodiments, more S/H converters and A/D converters may be added to achieve any arbitrary number of samples per subset.

Sampling techniques that operate at a rate less than twice the highest frequency component are understood to be sub-Nyquist rate sampling. Of course, in embodiments where sub-Nyquist rate sampling is utilized (i.e., one or more intervening sampling instants are skipped during the subset acquisition), the resulting samples are interleaved by the synthesizer 334 to obtain the desired sample sets representative of the entire echo characteristic.

In some embodiments, improvements in the signal to noise ratio (SNR) can be obtained by using higher sampling rates. For example, the sampling rate can be more than doubled and will still operate perfectly well in the majority of clinical situations. Notice also that the discussion of minimum sampling rates relates to the highest frequency present to any significant extent rather than the center frequency of the ultrasound being used.

In an alternative embodiment, the circuitry of FIG. 2 may be utilized to obtain multiple samples per subset. In this embodiment, the S/H circuits 218, 220, 222, 224, may operate two or more times per iteration. Preferably, they are operated at a rate lower than the desired effective rate, and typically at a sub-Nyquist rate.

In one exemplary embodiment providing a frame rate of 8 frames per second, and providing a 65×65 pixel image, and a 32×32 element array, then the DSP performs approximately 34.6 million complex multiply and add operations per second. Since each complex operation is equal to 4 real operations, the total computation cost is approximately 138.4 million operations per second. This level of computation can readily be performed by the Texas Instruments TMS320VC5416-160 which is a low power programmable DSP currently selling for less than $40. The addition of a second DSP (or faster DSPs when they are available) would enable higher frame rates, color flow imaging, and a variety of other signal processing applications. The systems described herein reduces overall cost by placing analog and mixed signal components in a custom IC, while using off-the-shelf programmable DSPs to implement rapidly evolving beamforming and signal processing algorithms.

Figure 4:
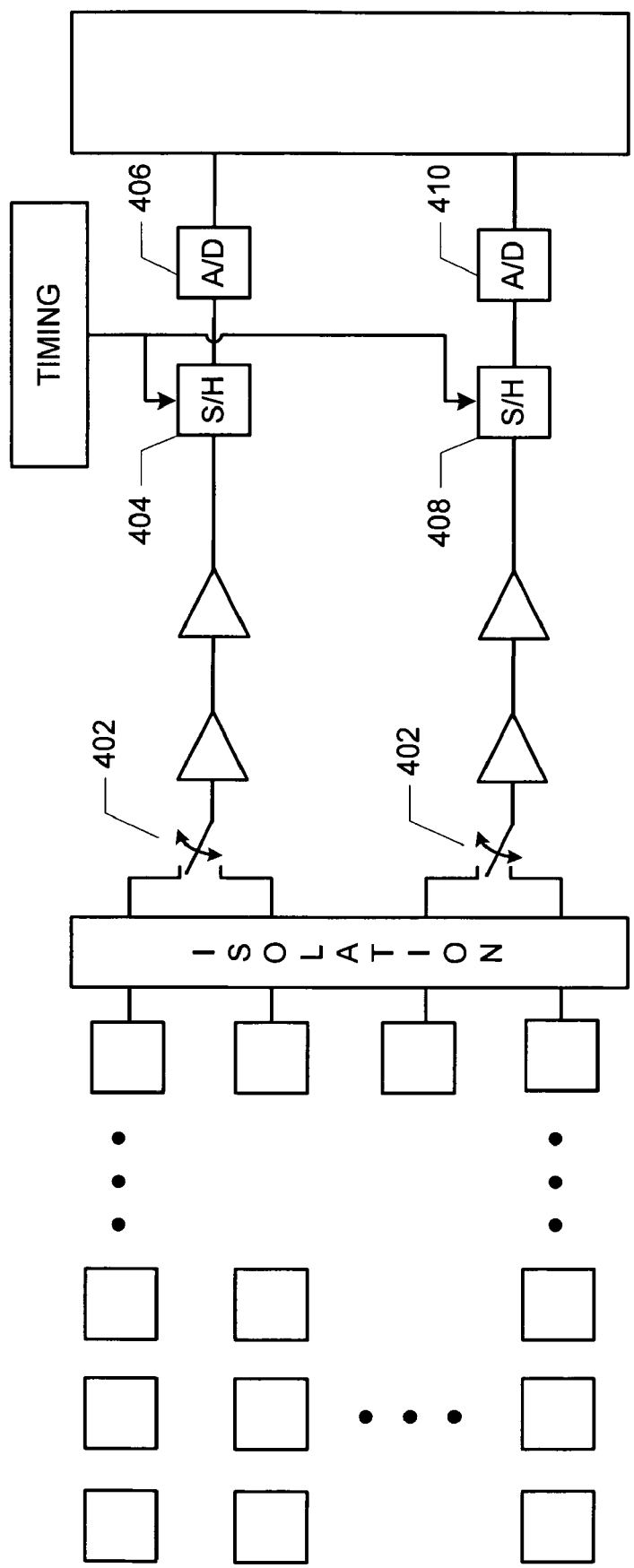
FIG. 4 is a block diagram depicting an alternative embodiment of the sampling hardware wherein the hardware resources are shared among a plurality of elements.
Figure 5:
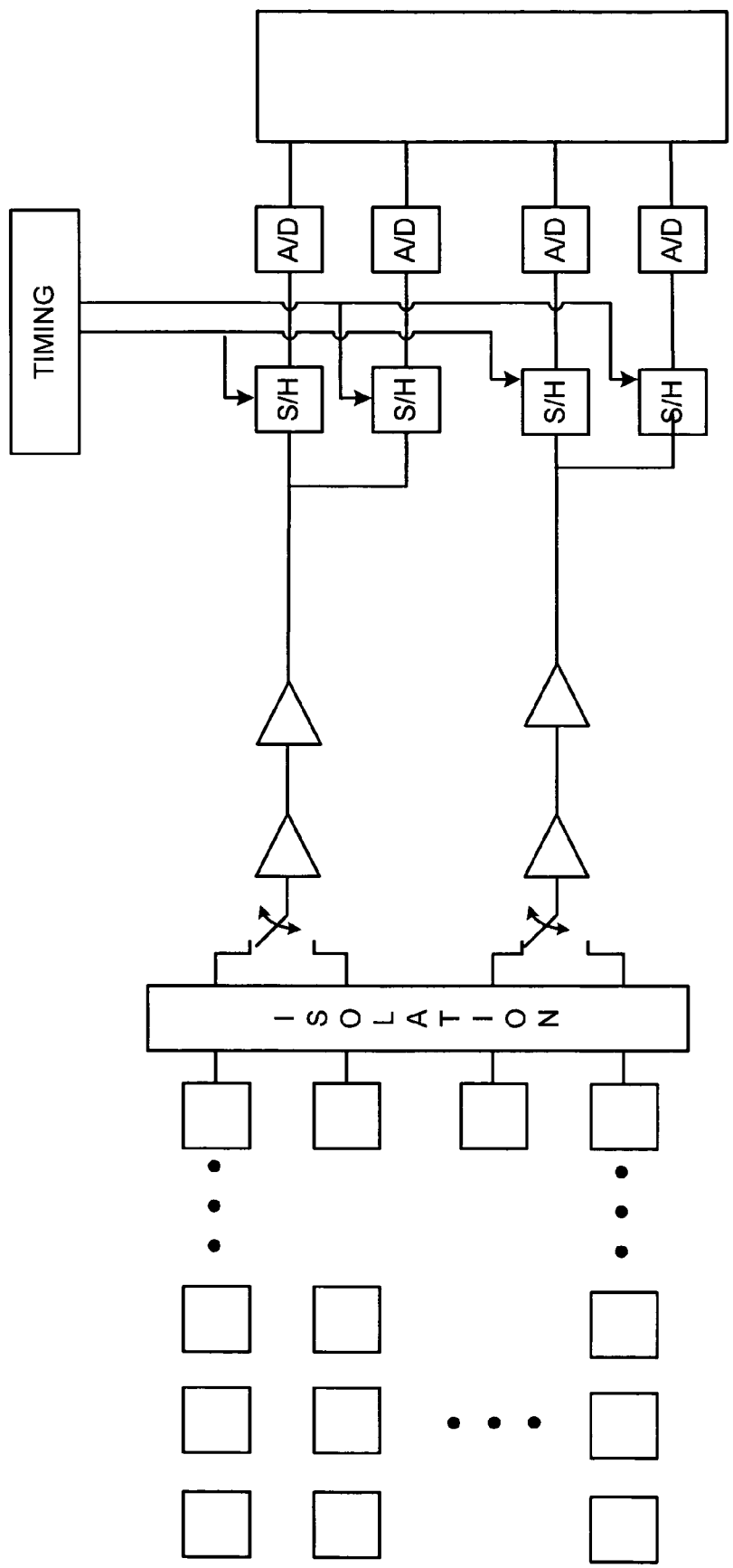
FIG. 5 is a block diagram depicting an alternative embodiment of the sampling hardware wherein the hardware resources are shared among a plurality of elements, and the sampling hardware may obtain either approximate complex samples (DSIQ) or multiple samples per subset.

In the embodiment shown in FIG. 4, the receive channels are selectively connected via switches 402 to shared data conversion hardware resources, including the S/H circuitry and A/D circuitry 404/406 and 408/410. In this manner, the hardware may be further simplified, with the result being that more iterations must be performed because samples are obtained at each iteration from only some array elements (those connected to the shared resources). Similarly, the embodiment shown in FIG. 5 may be used to obtain a single complex value using shared hardware resources, or may be configured to provide two real samples per iteration. The number of S/H and A/D elements may be increased to provide additional samples per iteration, and the A/D elements may be further shared among individual S/H elements. When sharing hardware resources, the number of array elements used in a given iteration depends on how many elements are assigned to a single converter. This is also referred to as a hardware reuse factor. For example, a hardware reuse factor of two means that two elements share resources, and thus one half the elements are able to obtain sample subsets during any given iteration.

As shown in FIGS. 7A-D, at each iteration only a portion, or subset, of the echo characteristic is sampled and stored. During the iterations, the portion of the echo characteristic that is measured and sampled is varied by changing the relative sampling instants. That is, the time offset from the transmission to the respective sampling instant is varied. The sample sets representative of the entire echo characteristic are then compiled from the multiple subsets of the ultrasonic transmissions. Thus, rather than obtaining an entire set of echo samples needed for image processing from each echo, the method described herein performs data collection iterations by transmitting an ultrasonic pulse, and receiving a pulse echo at a plurality of array elements, and at each element, obtaining a pulse echo sample subset at a respective time offset, wherein the time offset is varied. Then, for each of the relevant array elements, the sample subsets are used to compile a single synthesized composite pulse echo sample set that is representative of an echo characteristic at that element.

Figure 7A:
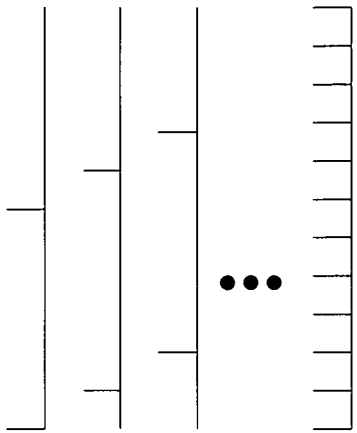
FIG. 7 is a timing diagram showing various embodiments of the sampling operation.

In one embodiment shown in FIG. 7A, the pulse echo sample subset contains a single sample. The single sample may be a real valued sample, or may be a complex valued sample obtained from two real samples separated by a quarter period of the echo signal. The period referred to here corresponds to the period of the center frequency of the echo signal. Since this is time sampling example, the sampling interval corresponds to one quarter of a period as measured at the center frequency. Center frequency can be defined in a number of ways but is generally associated with the frequency mid way between two cutoff thresholds—e.g. the lower and upper −6 dB levels with respect to peak spectral component. Other definitions of center frequency can be used. Center frequency here generally relates to the anticipated center frequency after receive transduction to an electrical signal—i.e. net of tissue and transducer related spectral shaping and frequency downshifting.

Figure 7C:
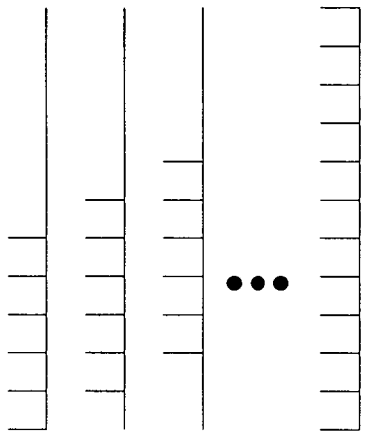
Figure 7B:
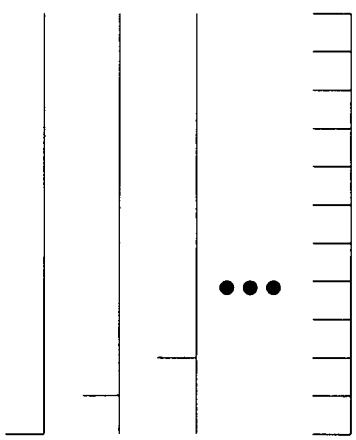

Alternatively, the subset may be a plurality of samples, as shown in FIG. 7B. A subset having a plurality of samples may be obtained by full-rate sampling of the echo signal for a portion of the echo. In this embodiment, each subset contains no more than half the desired samples. The multiple full-rate samples may be obtained, as described herein, from a plurality of A/D converter hardware resources, or a single full-rate converter that is only capable of providing a few consecutive samples. In one preferred embodiment, each subset contains no more than six consecutive samples.

In an alternative embodiment shown in FIG. 7C, the plurality of samples in one subset may be obtained by sub-Nyquist rate sampling. That is, samples may be obtained from a single echo signal at rate below the Nyquist rate. In subsequent iterations, samples (also at a sub-Nyquist rate) may be obtained, where the sampling instants have a different time offset. In both cases (successive sampling or sub-Nyquist sampling), the subsets are then combined to obtain to a full-length sample set representing the echo characteristic, sampled at an effective rate of at least the Nyquist rate. Thus, the number of desired samples in the sample set is simply the number of iterations times the number of samples obtained per iteration. For example, if a desired characteristic echo sample set is length N samples, and the number of data collection iterations is j, then the number of samples in each pulse echo sample subset is an integer equal to approximately N/j.

For embodiments using successive sampling, the sample subsets are concatenated into a single record for each element, whereas for embodiments using sub-Nyquist sampling, the sample subsets are interleaved to obtain the full echo characteristic sample record. The beginning and ending time offsets are determined in large part by the tissue depth of the desired image.

The step of synthesizing the pulse echo sample subsets of varied offsets into a single composite pulse echo sample set may be performed by concatenation or interleaving, as shown in FIGS. 7A, B, and C. The synthesizing step may also include manipulating the sample subsets in response to at least one motion estimation value as well as the respective time offsets used to gather the data.

In this regard, one or more array elements may be used to obtain samples used for motion estimation. A single motion estimation value may be obtained from individual direct-sampled complex echo samples taken over a plurality of iterations from a single element, each sample having the same time offset.

Comparisons of successive captures of this complex sample may be used to determine whether there has been significant motion. Specifically, motion may be estimated by a phase shift in the sampled data. If there is significant motion, one preferred embodiment causes the system to wait and try again in the expectation that motion will stop for a sufficiently long time for a 'good' acquisition set to be obtained.

Alternatively, the number of samples acquired can be adjusted downwards if there is some motion detected. In this manner, the record length may be adaptive, in that samples are taken over a shorter time period in the presence of motion. This corresponds to using the technique with a large f/number and hence getting a slightly inferior resolution. However, motion related problems will be mitigated. Another alternative implementation uses the signal acquired in common among acquisitions as a method to quantify the motion between transmissions. If the motion is fairly uniform over the tissue region being interrogated then the samples may be manipulated to compensate for the motion, such as by rotating the phases of successive acquisitions, or by interpolating the samples.

It is understood by those of skill in the art that propagation delay compensation may involve delays at offsets other than an integer number of sample offsets, and that well-known interpolation techniques (often a combination of interpolation followed by decimation) are used to generate the required samples.

In one embodiment, the axial motion estimate may be used in the synthesizing step. In particular, an approximation to the required re-interpolation could be simply achieved by skewing the timing of the triggering of successive samples from timing sources 236/336 to provide the compensation in the pre sampling domain. In this way, apart from initial motion estimation, all subsequent compensation does not need an interpolation step since it is inherently 'resampled' by virtue of the skewed sampling used.

One example of fine tuning the triggering interval to provide the equivalent of sampling with no tissue motion is as follows: if the detected motion estimate determines that successive echoes are 0.05 microseconds closer than the previous ones, then the sampling trigger is reset to 0.05 microseconds earlier on successive captures (0.05 ms, 0.10 ms, 0.15 ms, etc.). In embodiments using irregular transmit pulse spacing, the triggering can be scaled appropriately.

Figure 7D:
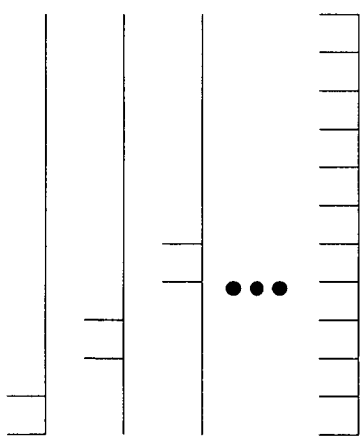

In an alternative embodiment shown in FIG. 7D, echo sample subsets that overlap in time may be gathered at each iteration. That is, the time offsets at each iteration are adjusted such that the relative sampling instants have substantial overlap. In this way, the synthesized echo record may be compiled from the subsets, and in addition, consecutive echo sample subsets may be used to estimate motion. Motion may be estimated using any one of a number of different techniques know to those of ordinary skill in the art, including cross-correlation, spline-based estimation, phase rotation, Fourier-based correlation matching, zero-crossing matching, etc. This data collection mechanism may be used at a single array element, at regional array elements, or all array elements.

Furthermore, with overlapping time offsets, signal averaging may be utilized to reduce the impact of non-coherent additive noise.

Alternatively, multiple motion estimation values may be derived from samples taken from elements that are at different locations within the array. In this manner, the motion may be evaluated for different regions of the array to accommodate tipping of the array as might occur when pressed against the tissue to be imaged. These may be referred to as regional motion estimation values. The regional motion estimation values may then be used to generate array-element specific motion estimation values.

In addition, the compact imaging device preferably includes a button to trigger image capture. Preferably a delay is interposed before image capture is initiated so that motion possibly associated with the pressing of the button will have ceased (typically after 200 to 500 milliseconds).

However obtained, the motion estimation value(s) may be used to enable/disable image processing to prevent the display of distorted images caused by excessive motion. Alternatively, the motion estimation value(s) may be used to alter or manipulate the data samples when forming the synthesized echo response characteristic in order to compensate for the motion.

Figure 8:
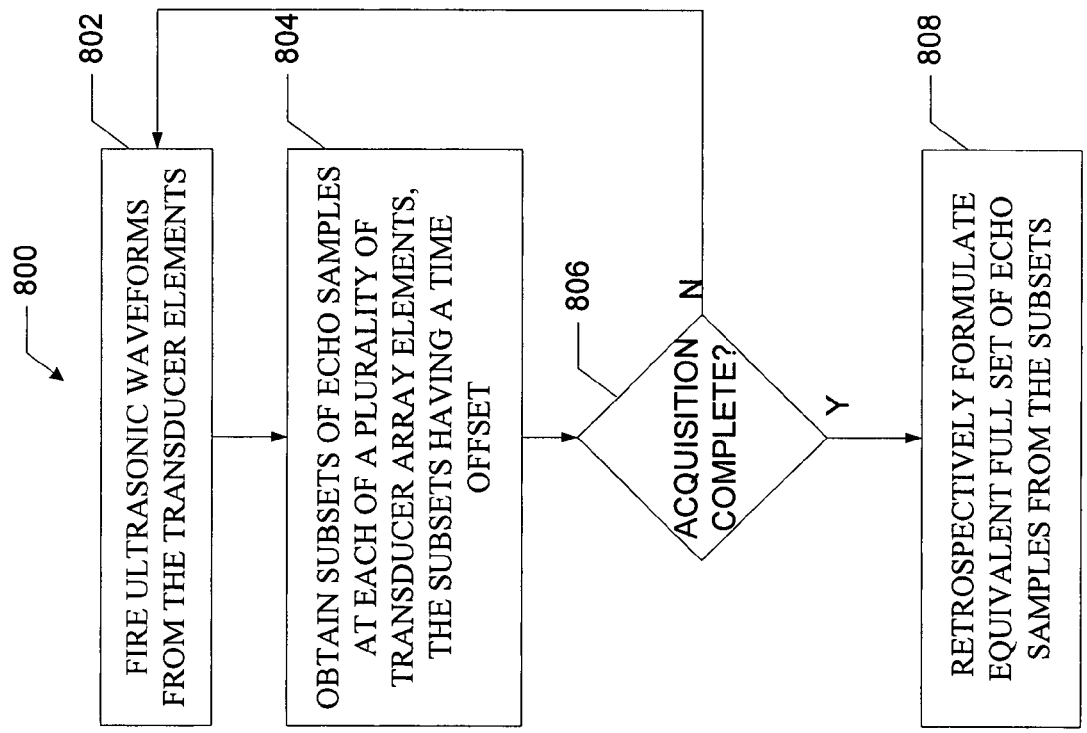
FIG. 8 is a flow diagram depicting one preferred method of the invention.

One preferred method 800 is described with respect to FIG. 8. At step 802, an ultrasonic transmit array is used fire ultrasonic waveforms from the transducer elements; after each transmit firing, at step 804 a subset of echo samples of an ultrasonic echo is obtained at each of a plurality of transducer array elements. Each subset is a portion of a desired echo response as determined by a time offset. The transmit firing and subset sampling is iteratively performed until all the desired samples have been obtained, as determined by block 806. At step 808, an equivalent full set of echo samples is retrospectively formulated from the subsets for each of the plurality of transducer array elements.

The devices and methods described herein provide very good resolution C-Mode (or B-Mode if desired) imaging when there is no tissue motion. However, when considering shallow C-Mode imaging, the ability to operate at a higher pulse repetition rate than is normally used in deep tissue B-Mode imaging provides for faster data acquisition, minimizing the effects of motion. Hence, relatively high frequencies with correspondingly rapid signal attenuation are desired. Additionally, since C-mode imaging involves forming images at a single depth, 'reverberation' (multi-path) artifacts from previous firings are statistically less likely to inject themselves within the reconstructed image plane than is the case in B-Mode imaging.

In some preferred embodiments, the transmit pulses may occur at non-uniform intervals. To obtain the desired sample subset, it is only necessary that the receive trigger is locked to the transmit event. It is not required that the transmit event follows a simple pattern. A non-uniform pulse pattern has the benefit of minimizing secondary echo artifacts. That is, residual echoes from previous transmit pulses that contribute to the measured echo from the present pulse will tend to cancel out in the later beamforming processing steps. Thus, different pulse intervals help make residual echos non-coherent over successive firings. The pulse intervals are preferably varied in a random or pseudorandom range of up to ±20%.

The complete system need only be slightly larger than the transducer itself, allowing placement of an LCD (or other flat, low profile) display directly over the transducer. This will facilitate familiarity for new users and improve the utility of ultrasound for guiding invasive procedures such as catheter insertion.

One application for the techniques described herein is for guiding needles for venous access. A secondary application is for biopsy guidance. In each case, the application generally involves a shallow imaging depth. The roundtrip propagation time through tissue to 20 mm is 26 microseconds (μs). Transmit pulses and sample acquisition is preferably performed at a rate of one per 40 μs. In most diagnostic ultrasound the line firing rate is significantly slower than this since the imaging depth is generally greater, and the probability of artifactual residual echo signals being superimposed within the reconstructed image are greater. Furthermore, it is desired that the highest practical frequency be used in any clinically usable product and that the intensity of the transmitted signal be attenuated if required to balance the need for SNR at the focal region of interest versus the desire to dissipate ultrasound signals potentially arising from deeper reflectors in the tissue, minimize transducer heating and prolonging battery life.

f/1.1 imaging (i.e. the entire aperture in this example) is used to obtain the highest possible resolution. This implies a maximum path difference for focusing of 1.93 mm. (for embodiments using receive-only beamforming only one-way path differences are used). At a speed of sound of 1540 m/s the required focal delay difference between the center of the array and the farthest active edge of the array is 1.25 μs. At an operating frequency of 5 MHz, this corresponds to just over 6 periods. Preferably, additional samples are taken to fully encompass the RF pulse associated with the finite bandwidth echo from a single idealized point target. For example, a transducer pulse echo signal −6 dB fractional bandwidth of approximately 30% may be used, and thus may add approximately 4 cycles of acquisition time to fully encompass the anticipated pulse and to provide for slice thickness integration in the final image. Thus, approximately 10 cycles worth of data are required to yield data to enable a conventional delay and sum beamforming operation for a single C-Mode plane.

In preferred embodiments, the effective sampling rate is 40 MS/s, which is significantly higher than required by the Nyquist criterion. Thus, 80 samples are required per data record. If each transmit/receive firing occupies 40 μs, the time duration for 80 samples to be acquired using the current approach is 3.2 ms. Clearly, it is also possible to operate closer to the Nyquist limit and thereby reduce the total acquisition time and reduce tissue motion effects.

Motion of the transducer relative to static tissue may be restrained to less than 1 mm/s in the beam axis dimension. Thus, in the time it takes to acquire a complete set of 80 samples, total target motion is 3.2 μm which is significantly less than a wavelength (0.31 mm). Even when 10 mm/s motion is present, and a longer time per acquisition is used (e.g. 80 μs), motion is still small compared with realistic wavelengths. The SAA approach may not be suitable for tissue regions in which there is a considerable motion—such as moving blood.

The parameters discussed above are set forth in Table 1.

TABLE 1

System Parameters

| | |
|---|---|
| Center Frequency | 5 MHz |
| Fractional −6 dB bandwidth | 30% |
| f/# | 1.1 |
| Number of Elements | 60 |
| Element center-center pitch | 0.3 mm |
| Apodization | Quartic Root Hann |
| Target | Idealized wire at 20 mm depth |

The Quartic Root Hann filter is used so as to 'fatten' the aperture, with respect to that obtained using a simple Hann window, and thus slightly tighten main lobe resolution and increase SNR at the expense of increased sidelobe level.

Exemplary embodiments of the invention have been described above. Those skilled in the art will appreciate that changes may be made to the embodiments described without departing from the true spirit and scope of the invention as defined by the claims.

We claim:

1. A method of obtaining a plurality of pulse echo sample sets at a plurality of ultrasonic transducer array elements, each pulse echo sample set being representative of an echo characteristic for use in ultrasound imaging using propagation delay compensation signal processing; the steps comprising:
   (i) performing data collection iterations by transmitting an ultrasonic pulse, and at each iteration:
      (a) receiving a pulse echo at a plurality of array elements, and
      (b) at each of the plurality of array elements, obtaining a pulse echo sample subset at a respective time offset, wherein the time offset is varied between successive iterations; and
   (ii) for each of the plurality of array elements, aggregating the pulse echo sample subsets of varied offsets into a single synthesized composite pulse echo sample set that is representative of an echo signal.

2. The method of claim 1 wherein the pulse echo sample subset is a single sample.

3. The method of claim 1 wherein the pulse echo sample subset is a single complex sample.

4. The method of claim 1 wherein the pulse echo sample subset contains a number of samples less than or equal to one half the number of samples in the pulse echo sample set.

5. The method of claim 1 wherein each pulse echo sample set is an integer N samples long, and the number of data collection iterations is j, and wherein the number of samples in each pulse echo sample subset is an integer equal to approximately N/j.

6. The method of claim 1 wherein the step of obtaining the pulse echo sample subset is performed by sampling the pulse echo at a sub-Nyquist sampling rate, and wherein the step of aggregating the pulse echo sample subsets is performed by interleaving the samples from the pulse echo sample subsets.

7. The method of claim 1 wherein the plurality of array elements is substantially all the elements in the array.

8. The method of claim 1 wherein the pulse echo sample subsets are obtained using shared sampling hardware resources, and wherein the plurality of array elements are a fraction of all the elements in the array, wherein the fraction is determined by a hardware reuse factor.

9. The method of claim 1 wherein at least one motion-detection sample is obtained at each iteration.

10. The method of claim 1 wherein the smallest time offset is determined by a desired target depth.

11. The method of claim 1 wherein the step of aggregating the pulse echo sample subsets into a single synthesized composite pulse echo sample set comprises manipulating the sample subsets in response to at least one motion estimation value and the respective time offsets.

12. The method of claim 11 wherein the at least one motion estimation value is obtained from a plurality of individual direct-sampled complex echo samples taken over a plurality of iterations, having the same time offset.

13. The method of claim 1 wherein at each of the plurality of array elements, the pulse echo sample subsets at consecutive iterations overlap in time.

14. The method of claim 13 wherein the pulse echo sample subsets from consecutive iterations are used to generate at least one motion estimation value.

15. The method of claim 1 further comprising the step of determining at least one motion estimation value.

16. The method of claim 15 wherein the at least one motion estimation value comprises a plurality of regional motion estimation values for different regions of the array.

17. The method of claim 16 wherein the regional motion estimation values are used to generate array-element specific motion estimation values.

18. The method of claim 1 wherein the time offsets used for each element are varied in accordance with collecting data for producing an image of a plane that is non-parallel to the transducer array.

19. The method of claim 1 wherein the step of transmitting an ultrasonic pulse comprises transmitting a plane wave using all the transducer elements.

20. The method of claim 1 wherein the step of transmitting an ultrasonic pulse comprises transmitting a plane wave using a subset of the transducer elements.

21. The method of claim 1 wherein the step of transmitting an ultrasonic pulse comprises using at least a subset of elements transmitting to a selected focal zone.

22. The method of claim 1 wherein the time interval between successive transmit pulses is varied for at least some iterations.

23. A method collecting ultrasonic echo samples for use in ultrasonic image processing, comprising the steps of:
performing multiple transmit firings of ultrasonic waveforms from an ultrasonic transducer array of transducer elements;
after each transmit firing, obtaining a subset of echo samples of an ultrasonic echo at each of a plurality of transducer array elements, wherein each subset is a portion of a desired echo signal as determined by a time offset;
retrospectively formulating an equivalent full set of echo samples from the subsets for each of the plurality of transducer array elements.

24. The method of claim 23 wherein the subset of echo samples are obtained by sampling the ultrasonic echo at a sub-Nyquist sampling rate.

25. The method claim 23 wherein the step of retrospectively formulating an equivalent full set of echo samples is performed in response to a motion estimation value.

26. The method claim 23 wherein the step of retrospectively formulating an equivalent full set of echo samples from the subsets is performed by concatenating samples from the subsets from the respective elements.

27. The method claim 23 wherein the step of retrospectively formulating an equivalent full set of echo samples from the subsets is performed by interleaving samples from the subsets from the respective elements.

28. The method claim 23 wherein the time offset is adjusted in response to at least one motion estimation value.

29. The method of claim 23 wherein a time interval between the multiple transmit firings is not constant.

30. A method collecting ultrasonic echo samples for use in ultrasonic image processing, comprising the steps of:
performing multiple transmit firings of ultrasonic waveforms from an ultrasonic transducer array of transducer elements;
at each of a plurality of transducer array elements, obtaining a plurality of sample subsets of echo samples, wherein each subset is a portion of a desired echo signal;
for each of the plurality of transducer array elements, synthesizing an equivalent full set of echo samples at a desired effective sampling rate from each of the plurality of subsets.

* * * * *

UNITED STATES PATENT AND TRADEMARK OFFICE
CERTIFICATE OF CORRECTION

PATENT NO.         : 8,057,392 B2                                          Page 1 of 1
APPLICATION NO.    : 11/245266
DATED              : November 15, 2011
INVENTOR(S)        : Hossack et al.

It is certified that error appears in the above-identified patent and that said Letters Patent is hereby corrected as shown below:

In the specification
In column 1, line 7-9, delete "The United States Government may have acquired certain rights in this invention pursuant to Grant No.: EB02349 awarded by the National Institutes of Health (NIH)." and insert --This invention was made with government support under EB002349 awarded by the National Institutes of Health. The government has certain rights in the invention.--, therefor Signed and Sealed this
Thirty-first Day of May, 2016

Michelle K. Lee
*Director of the United States Patent and Trademark Office*